United States Patent
Glaug et al.

(10) Patent No.: US 11,752,755 B2
(45) Date of Patent: Sep. 12, 2023

(54) INLINE HIGH-SPEED MANUFACTURING AND PRINTING OF ABSORBENT PRODUCTS

(71) Applicant: Drylock Technologies NV, Zele (BE)

(72) Inventors: Frank Glaug, Eau Claire, WI (US); Ricardo Borrero, Eau Claire, WI (US); Michael Sandor, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 193 days.

(21) Appl. No.: 16/639,677

(22) PCT Filed: Aug. 18, 2017

(86) PCT No.: PCT/IB2017/055007
§ 371 (c)(1),
(2) Date: Feb. 17, 2020

(87) PCT Pub. No.: WO2019/034918
PCT Pub. Date: Feb. 21, 2019

(65) Prior Publication Data
US 2020/0276798 A1 Sep. 3, 2020

(51) Int. Cl.
*B41F 5/24* (2006.01)
*A61F 13/15* (2006.01)
(Continued)

(52) U.S. Cl.
CPC .......... *B41F 5/24* (2013.01); *A61F 13/15772* (2013.01); *A61F 13/51496* (2013.01);
(Continued)

(58) Field of Classification Search
CPC .. B41F 5/24; B41F 13/02; B41F 13/60; B41F 17/005; A61F 13/15772; A61F 13/51496;
(Continued)

(56) References Cited

U.S. PATENT DOCUMENTS

| 7,178,571 B2 | 2/2007 | Vergona |
| 2005/0092427 A1* | 5/2005 | Vergona .................. A61F 13/42 156/250 |

(Continued)

FOREIGN PATENT DOCUMENTS

WO WO-2011022537 A1 2/2011

OTHER PUBLICATIONS

"International Application Serial No. PCT/IB2017/055007, International Search Report dated Apr. 9, 2018", (dated Apr. 9, 2018), 6 pgs.
"International Application Serial No. PCT/IB2017/055007, Written Opinion dated Apr. 9, 2018", (dated Apr. 9, 2018), 9 pgs.

*Primary Examiner* — David H Banh
(74) *Attorney, Agent, or Firm* — Schwegman Lundberg & Woessner, P.A.

(57) ABSTRACT

The present invention methods for manufacturing absorbent articles that involve the placement of absorbent cores having variable absorbency levels on consecutively aligned absorbent articles within the same manufacturing line. Additionally, the present invention also includes the provision of single packages of disposable absorbent articles that contain a first absorbent article having a first absorbency level and a second absorbent article having a second absorbency level, wherein the second absorbency level is higher than the first absorbency level.

15 Claims, 14 Drawing Sheets

(51) Int. Cl.

|         |           |
|---------|-----------|
| *A61F 13/514* | (2006.01) |
| *A61F 13/551* | (2006.01) |
| *A61F 13/84*  | (2006.01) |
| *B41F 13/02*  | (2006.01) |
| *B41F 13/60*  | (2006.01) |
| *B41F 17/00*  | (2006.01) |

(52) U.S. Cl.
CPC ............ *A61F 13/551* (2013.01); *A61F 13/84* (2013.01); *B41F 13/02* (2013.01); *B41F 13/60* (2013.01); *B41F 17/005* (2013.01); *A61F 2013/8497* (2013.01)

(58) Field of Classification Search
CPC . A61F 13/551; A61F 13/84; A61F 2013/8497
See application file for complete search history.

(56) References Cited

U.S. PATENT DOCUMENTS

| 2006/0069372 | A1* | 3/2006  | Chakravarty ......... A61F 15/001 604/385.02 |
| 2006/0158505 | A1* | 7/2006  | Jin ............................. B41J 2/32 347/171 |
| 2006/0247594 | A1  | 11/2006 | Nickel et al. |
| 2010/0089264 | A1  | 4/2010  | Warner |
| 2011/0028929 | A1  | 2/2011  | Hopkins et al. |
| 2011/0094674 | A1* | 4/2011  | Oetjen ................. A61F 13/472 156/277 |
| 2013/0014475 | A1* | 1/2013  | Chakravarty ..... A61F 13/15804 53/474 |
| 2017/0225460 | A1* | 8/2017  | Strasemeier ......... B41J 2/04586 |

\* cited by examiner

INLINE HIGH-SPEED MANUFACTURING AND PRINTING OF ABSORBENT PRODUCTS

PRIORITY APPLICATION

This application is a U.S. National Stage Filing under 35 U.S.C. 371 from International Application No. PCT/IB2017/055007, filed on Aug. 18, 2017, and published as WO2019/034918 on Feb. 21, 2019; the benefit of priority of which is hereby claimed herein, and which application and publication are hereby incorporated herein by reference in its entirety.

FIELD

The present disclosure relates generally to high-speed inline manufacturing and printing of disposable absorbent articles having different absorbency levels, such as adult briefs, adult underwear, baby diapers, children training pants, incontinence pads, feminine care pads, baby changing pads, furniture pads, under pads, wound care, and the like.

BACKGROUND

There are several types of commercially available products for the absorption of bodily fluids. Such absorbent products are available in different types, designs, colors, and dimensions, each one having one or more unique features. For example, both adult incontinence products and baby diapers are available in different colors/patterns and offer day and night products, the night products having a higher absorbency level. Additionally, tiered absorbency level products are available for feminine hygiene and adult incontinence products. However, limitations exist on the ability to provide variation in absorbency levels, as well as variation in the images printed on the products, within the context of high speed automated manufacturing processes.

Absorbent products are currently manufactured and packaged using fully automated high-speed inline processes. However, automatically manufacturing and packaging different absorbency levels together on the same manufacturing line without requiring an additional repacking operation has not been achievable. Typically, separate manufacturing runs are made for each absorbency level and the products are packaged separately, such that consumers desiring multiple absorbency level products must purchase each product separately. This is often both inconvenient and costly for the consumer who must buy an entire package of one absorbency level, as well as an entire package of a different absorbency level, even though such quantities may not be needed. In addition, smaller stores (such as drug stores) have limited shelf space. It is difficult for them to stock the store shelves with bulky products, such as adult briefs and/or underwear, that have different sizes (small, medium, large, extra-large, double XL), different genders (male, female, unisex), different absorbency levels (moderate, maximum, etc.) and different lifestyles (day, night, etc.). Accordingly, it would be preferred by these small stores to offer multi-packs, such as day and night products in one package, rather than separate packages.

With respect to the printing of absorbent articles during high-speed inline processes, prior to the present disclosure, automatically printing and packaging different colors and/or patterns together on the same manufacturing line without requiring an additional repacking operation has not been achievable. Typically, printing is done separate from the manufacturing lines, with rolls of preprinted substrates being provided to the manufacturing lines. The separate operations of printing and absorbent article manufacturing can lead to increased costs associated with, for example, shipping, storing, and handling. Further, each roll would be limited to just one pattern, per machine, which could be continuous in pattern or registered. There is also a limit on the number of colors you can choose. Additionally, prior to this disclosure, those methods which combine printing and manufacturing operations in an attempt to print more than one image only had the ability to print a plurality of first images consecutively and a plurality of second images consecutively, the two sets of images separated by a large blank space on the substrate. These methods resulted in the loss of product and excess waist, and were limited in the variety of color and/or images that could be printed and packaged.

Given these limitations, the only way to provide a single package containing absorbent articles having different images and colors using these prior art methods was to repackage the different absorbent articles. Thus, there exists a need to manufacture absorbent articles having variable absorbency levels, and different images printed thereon, on the same production line at the same time frame.

SUMMARY

The presently disclosed methods involve the manufacturing of absorbent articles having different absorbency levels and/or different images in succession. Generally, methods can include the insertion of extra layers of absorbency and/or the printing of different images at various intervals during the manufacturing process to produce absorbent articles having varying images and/or absorbent levels interspersed in the same manufacturing run.

Methods of the invention involve providing a substrate moving in the web direction at a first velocity, the substrate divided by pitch intervals, each pitch interval having a pitch length corresponding to a length or a width of an absorbent article prior to being cut. In aspects wherein different images are printed on the substrate in succession, images are printed on the substrate using a printer system as the substrate moves at a first velocity in the web direction, with each image separated by pitch intervals. The images printed include at least a first image and a second image, wherein the first and second images are printed within consecutive pitch intervals. In one aspect, the first image includes a first color while the second image includes a second color. However, the images are not limited to these colors. For example, each image can have several colors, some of which are the same.

The substrate can comprise any number of materials, such as a woven material, a non-woven material, a polymer-based film, a tissue wrap, a bilaminate composite, and an airlaid material. In one embodiment, the substrate is a non-woven material, such as a spunbond-meltblown-spunbound (SMS) material. In another aspect, the substrate can be the bottom sheet of the absorbent article, such that the image is visible from the outside when the absorbent article is on the wearer's body. In yet another embodiment, the substrate can be the top sheet, such that the image is on the surface of the absorbent article facing the wearer's body.

In order to facilitate even printing and a consistent appearance of the image throughout all of the absorbent articles, method of the invention also involve the provision of tension to the substrate. This tension provides the substrate with a smooth surface for printing as the substrate passes through the printer system. In one aspect, tension is provided by advancing the web over a vacuum drum as the substrate is printed.

The images can be printed using a number of printer system configurations. For example, the first and second images can both be printed using one set of printheads. Alternatively, the first image can be printed using a first set of printheads and the second image can be printed using a second set of printheads. Additionally, more than one set of printheads can be used to print both images. It is to be understood that the invention is not limited to two images and that any number of images can be printed, each being printed at consecutive intervals to one another as the substrate continues movement in the web direction using any one or combination of printhead sets. In one embodiment, the printhead sets are spatially separated from each other in the web direction.

In embodiments that include the use of a vacuum drum, the printing system is positioned around the vacuum drum such that the printheads extend in a radial direction and are separated by a predetermined distance from the outer surface of the vacuum drum. In the event that the printer system includes more than one set of printheads, each sequential set is spatially separated from the previous set in the web direction.

In operation, the printheads are controlled by one or more printer controllers, which are in turn connected to the controller for the manufacturing line. By connecting the printer controllers to the manufacturing line controller(s), printing operations are effectively coordinated with the remainder of the manufacturing operations. In one embodiment, printing is effectuated sending a start signal from the print controller to one or more sets of printheads. In the case of multiple sets of printheads, start signals can be sent to the sets simultaneously or at different times in order to stagger printing.

The method also contemplates curing the images subsequent to being printed. Curing will help to set the ink on the substrate. Curing can comprise any number of techniques, such as infrared heating or UV radiation. In one embodiment, the image is cured by applying heat and/or air flow to the substrate.

The method also contemplates providing a second substrate moving in a web direction on which images are to be printed. Similar to the first substrate, the second substrate would also be divided by pitch intervals and printed images would be separated by pitch interval.

The images printed using the methods and systems of the invention can be printed at speeds of at least 200 fpm. In one embodiment, the images are printed at a speed of at least 500 fpm. In another embodiment, the images are printed at a speed of at least 700 fpm. In one aspect, the images produced using the systems and methods of the invention have a resolution of about 600×600 dpi.

According to methods of the invention, the images are printed using pigment-based or solvent-based inks. In certain aspects, pigment-based ink is preferred due to its ability to provide scratch, fade and water resistance. In other aspects, the printing system is an inkjet-based system, such as a stream inkjet system.

In aspects wherein different absorbency levels are produced in succession, absorbent cores are provided to the substrate as the substrate moves in the web direction, each core being separated by a pitch interval. Specifically, a first absorbent core having a first absorbency level is provided to the substrate between a first pitch interval and a second pitch interval, and a second absorbent core having a second absorbency level higher than the first is provided to the substrate between the second pitch interval and a third pitch interval. In addition to the methods for manufacturing absorbent articles having variable absorbent levels, the present invention also includes the provision of single packages of disposable absorbent articles that contain a first absorbent article having a first absorbency level and a second absorbent article having a second absorbency level, wherein the second absorbency level is higher than the first absorbency level.

The absorbent cores can comprise any number of layers. For example, the first absorbent core can comprise a single layer and the second absorbent core can comprise at least two layers. In one embodiment, the first absorbent core comprises a single layer the second absorbent core comprises two layers. In another embodiment, the first absorbent core comprises a single layer and the second absorbent core comprises three layers. The first absorbent core can also, for example comprise two layers, while the second absorbent core comprises at least three layers.

In yet another embodiment, the first absorbent core and the second absorbent core each comprise one layer. The first absorbent core and the second absorbent core can also each comprise two layers.

For example, the first absorbent article can have a single layer absorbent core comprising pulp and SAP, while the second absorbent article can have a dual layer absorbent core, each layer comprising pulp and SAP. In a second example, the first absorbent article can have a dual layer absorbent core, each layer comprising pulp and SAP, while the second absorbent article can have a triple layer absorbent core, each layer comprising pulp and SAP. In a third example the first absorbent article can have a single layer absorbent core comprising an airlaid material, while the second absorbent article can have a dual layer absorbent core, each layer also comprising an airlaid material. In a fourth example, the first absorbent article can have a dual layer absorbent core each comprising an airlaid material, while the second absorbent article can have a triple layer absorbent core, each layer also comprising an airlaid material. In a fifth example, the first absorbent article can have a single layer absorbent core comprising pulp and SAP, while the second absorbent article can have a single layer absorbent core, comprising pulp, SAP, and an airlaid material. In a sixth example, the first absorbent article can have a dual layer absorbent core, each layer comprising pulp and SAP, while the second absorbent article can have a dual layer absorbent core, each layer comprising pulp, SAP, and an airlaid material. It is to be understood that the above embodiments are only provided as examples and not meant to be limiting. The absorbent cores can be any combination of the above materials, or any other material.

In one aspect, the methods further involve, prior to providing the first and second absorbent cores to the substrate, the steps of forming the first absorbent core into a first shape and forming the second absorbent core into a second shape. In yet another aspect, methods of the invention involve printing a first image on the substrate between the first and the second pitch intervals and optionally printing a second image on the substrate between the second and the third pitch intervals.

In one embodiment, the absorbent articles are marked using a label which can indicate the type of product (e.g., Night or Day absorbency levels) and/or the size (e.g., small S, Medium M, Large L, etc.). According to one aspect, methods of the invention involve providing a first label to the first absorbent product and providing a second label to the second absorbent product, wherein the first label is different from the second label.

In order to provide discrete absorbent articles, the substrate can be cut at the pitch intervals as the web advances. In certain aspects, the discrete absorbent articles are advanced along the manufacturing line to a packaging station and the discrete absorbent articles are packaged such that, for example, the first absorbent article comprising a first absorbent core and/or a first image is automatically packaged with the second absorbent article comprising a second absorbent core and/or a second image.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 7A depicts an image printed on only one half of the absorbent article. FIG. 7B depicts an image printed on both halves of the absorbent article. FIG. 7C depicts an image comprising a single color printed on an entire surface of a substrate.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The presently disclosed methods involve the manufacturing of absorbent articles having different absorbency levels and/or images in succession. Generally, methods can include the printing of different images and/or the insertion of extra layers of absorbency at various intervals during the manufacturing process to produce absorbent articles having varying images and/or absorbent levels interspersed in the same manufacturing run.

The absorbent articles to be manufactured in accordance with the present disclosure can include, but are not limited to adult briefs, adult underwear, baby diapers, children training pants, incontinence pads, feminine care pads, baby changing pads, furniture pads, under pads, wound care, and the like.

Figure 1:
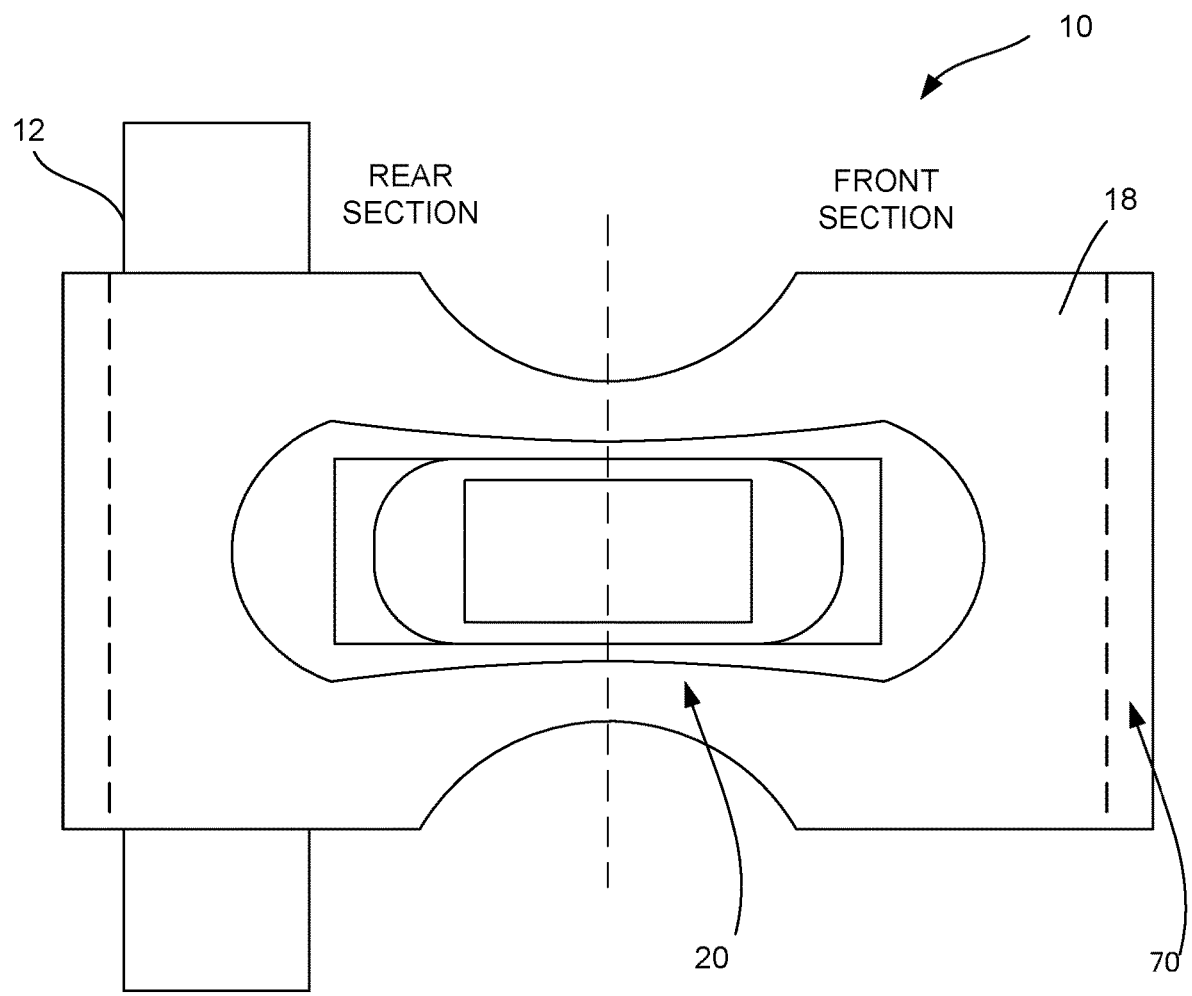
FIG. 1 is a top plan view of a disposable absorbent article consistent with the present disclosure.
Figure 2:
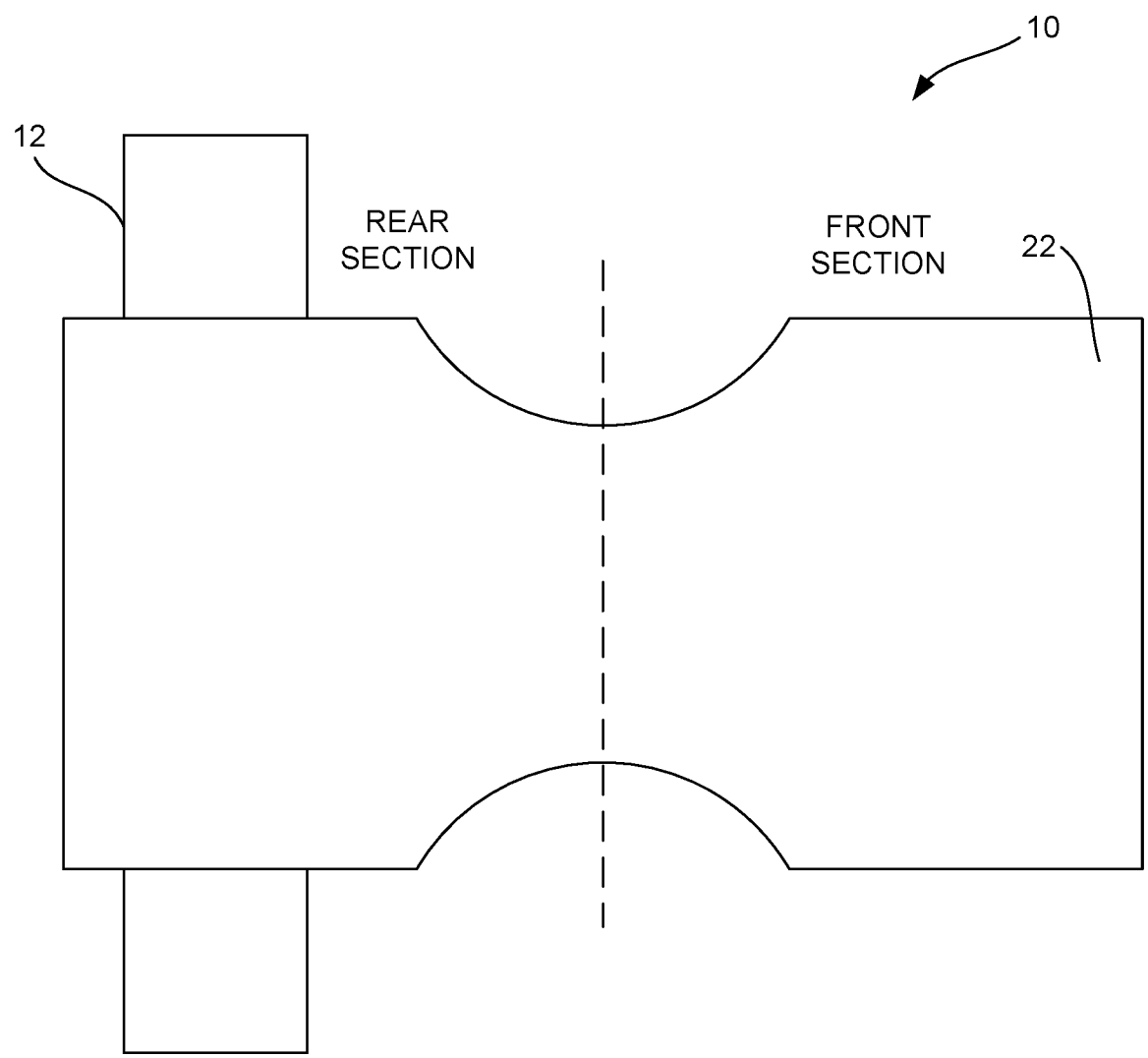
FIG. 2 is a bottom plan view of the absorbent article of FIG. 1

In one embodiment, the absorbent article is a disposable undergarment, such as an adult brief. FIG. 1 provides a top plan view of an exemplary disposable undergarment 10 and FIG. 2 provides a bottom plan view of the disposable undergarment. While the following description focuses on disposable undergarments with reference to the illustrated embodiments, it should be clear that the subject invention can be used for any type of absorbent article to be worn on a person's body for absorbing bodily fluids and/or excrement.

The undergarment 10 is shown in FIG. 1 from the interior side of the product that is designed to be in direct contact with the wearer, as opposed to the exterior side of the product, as shown in FIG. 2. The absorbent article 10 generally includes a front section and a rear section, wherein the front section is generally designed to be fitted against the front, or anterior portion, of a wearer, while the rear section is generally designed to be fitted against the rear, or posterior portion, of the wearer, such that front and rear sections generally oppose one another once fitted to the wearer. The absorbent article also includes a crotch region which encompasses the region in which the absorbent core is attached and spans both the front and the rear portions. The undergarment 10 can have various shapes and sizes, and is generally configured to be worn between an individual's legs and secured about the waist.

Figure 3:
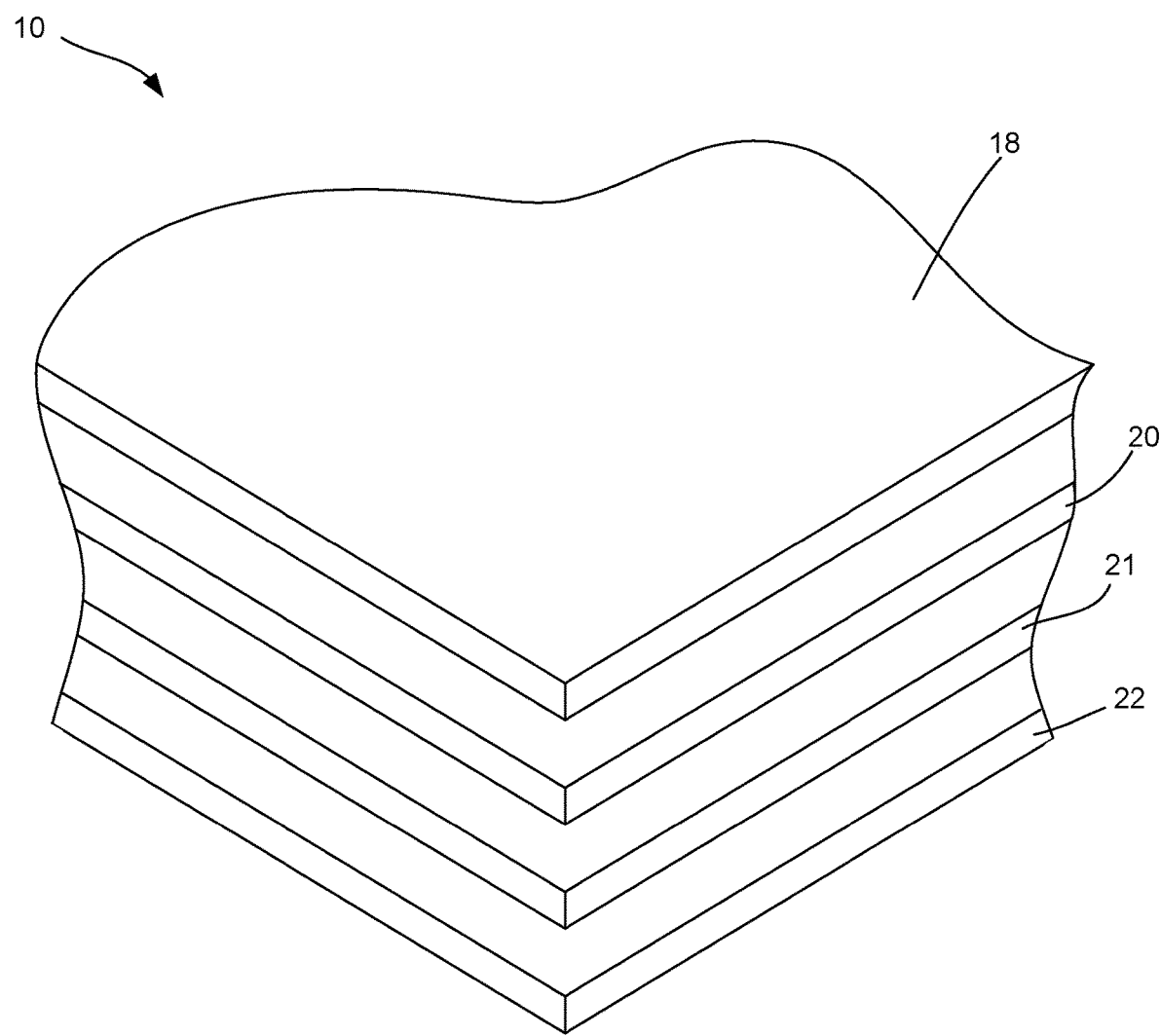
FIG. 3 is an enlarged perspective view of a portion of the absorbent article of FIG. 1 illustrating the multiple layers separated from one another

As shown in FIG. 3, the undergarment 10 may be constructed from multiple layers, which may include at least a first layer 18 and a second layer 20. The first layer 18, also referred to herein as the "top sheet 18", is generally configured to engage a subject's skin and allow a fluid from the subject (i.e., human, animal, etc.) to flow therethrough, at least in a direction away from the subject's skin. The second layer 20, also referred to herein as the "absorbent core 20", includes a fluid absorption and retention portion having at least one absorbent material for absorbing a fluid passing through the top sheet 18. In certain embodiments described herein, the undergarment 10 includes a third layer 21, also referred to herein as the "fluid impervious barrier 21". The absorbent core 20 is positioned between the top sheet 18 and the fluid impervious barrier 21. The fluid impervious barrier 21 may be breathable, not breathable, cloth-like or non-cloth-like and can comprise one or more materials that include, but are not limited to, polyethylene, polypropylene, polyester, nylon, polyvinyl chloride, and combinations thereof. The undergarment 10 further includes a fourth layer 22 coupled to the fluid impervious barrier 21. The fourth layer 22, also referred to herein as the "back sheet 22", generally serves as the outermost layer of the undergarment 10 that faces away from the wearer's body.

The back sheet 22 and the top sheet 18, both of which can serve as substrates upon which images are to be printed for purposes of the present methods, can be made of the same material or different material. The material is preferably a non-woven material. The back sheet 22 is generally formed from a nonwoven material, to provide a more underwear-like appearance and feel, and as well as a more cost-effective and comfortable alternative to conventional disposable undergarment designs. The top 18 and back sheets 22 can be comprised of, for example, non-woven fibers, such as polypropylene (PP), polyethylene (PE), polyethylene terephthalate (PET), bi-component fibers, polyester, cotton, cotton blend, viscose, rayon, etc. or any combination thereof; melt-blown nonwovens; spunlaid (spunlace) nonwovens, such as PP spunbounds and PET spunbounds; melt-blown and spunbound combinations (SM), including spun-melt-spun (SMS); and airlaid paper; or any combinations thereof. In some embodiments, the top sheet 18 can include a zone-coated surfactant or an apertured three-dimensional (3D) film.

In certain embodiments, either or both of the top sheet 18 and bottom sheet 22 can be combined with an elastomeric material to form an elastomeric composite. The elastomeric material can be a stretch adhesive, such as Conforma 9534-62-1 available from H.B. Fuller Company in Vadnais Heights, Minn. See U.S. Patent Application No. 62/432,851, incorporated herein by reference in its entirety.

In order to secure the undergarment onto a wearer's body and stay in place, the undergarment can include a fastening system. As shown in FIGS. 1 and 2, the undergarment 10 can include tabs 12 extending from the rear section of the undergarment 10. Various attachment mechanisms (e.g., tabs 12) can be used, such as micro-hooks (e.g., Velcro), fastening tapes, and the likes. The attachment mechanisms can extend from one or both of the side edges on one or both of the front and back portions to attach to the opposite portion. For example, one or more micro-hooks can extend from the side edges of the back portion to engage with the front portion of the absorbent article 10.

Additionally, in one embodiment, the surface upon which the attachment means is to be attached can be modified to provide for an improved attachment surface. Improved attachment means are further described in co-pending provisional application titled "Improved Fastening System for Absorbent Articles", having application No. 62/432,729, and filed Dec. 12, 2016, the content of which is incorporated by reference herein in its entirety.

In other embodiments, a seal, such as an ultrasonic bond, can be provided along the side edges of the absorbent article instead of tabs to secure the front portion with the back portion.

The waistband 70 of the absorbent article, shown generally in FIG. 1, can include any number of options that provides for a tight fit and seal with the wearer's body. In one embodiment, the waistband consists mainly of the elastomeric composites. In other embodiments, as described in more detail in the provisional application titled "ELASTOMERIC PANEL ABSORBENT GARMENT", having application No. 62/337,111, and filed May 16, 2016, the content of which is incorporated by reference herein in its entirety, the waistband 70 can include any one or combination of laminate elastic film, stretch adhesive, and elastic strands.

Figure 4:
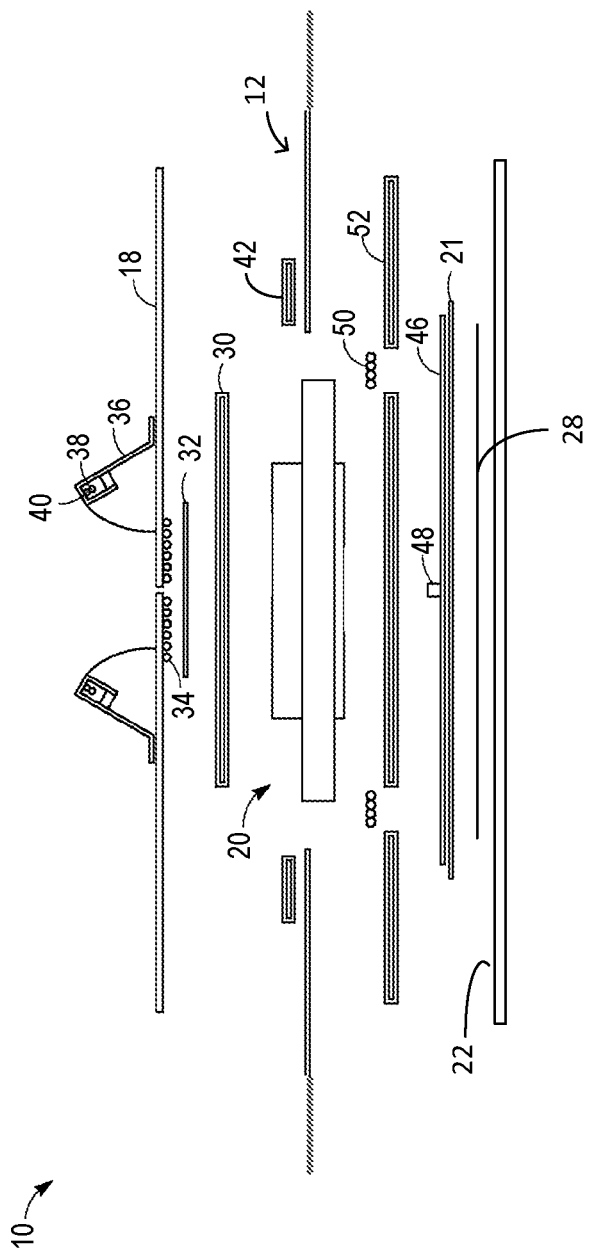
FIG. 4 is an exploded cross-sectional view of the absorbent article of FIG. 1 illustrating the various components.

FIG. 4 is an exploded cross-sectional view of the absorbent article 10 illustrating its various components, including the top sheet 18, absorbent core 20, fluid impervious barrier layer 21, and back sheet 22.

The absorbent core 20 is positioned within the crotch portion, as shown in FIG. 1, and is generally disposed between the top sheet 18 and the bottom sheet 22. As shown in FIG. 4, the top sheet 18 may be coupled to the joined to the absorbent core 20 via an adhesive 30. The absorbent core 20 can include an acquisition distribution layer 32 (or "ADL") and an absorbent layer (part of absorbent core 20), with the acquisition layer 32 disposed between the absorbent layer and the top sheet 18, as shown in FIG. 4. The acquisition layer 32 is responsible for distributing fluid across the absorbent layer for faster and more even absorbance, and to help provide a sense of dryness to the skin of the wearer. Exemplary acquisition distribution layer materials include, but are not limited to, through air bonded (TAB) nonwovens, "curly" fibers, 3D perforated plastic film, resin-bonded nonwovens, and "high loft" nonwovens. The ADL 32 can be coupled to the top sheet 18 with an adhesive 34.

The absorbent layer may generally include an absorbent material, a nonabsorbent material, or any combination thereof. Exemplary materials include, but are not limited to, one or more of fluff pulp, airlaid material (such asVH270.203 available from Glatfelter located in Pritzwalk, Germany), super absorbent polymer (SAP), tissue, cotton fibers, rayon viscose, creped tissue, paper towel, and curly fibers. In a preferred embodiment, the absorbent layer is an airlaid material.

The absorbent layer may be comprised of a single ply or multiple plies (i.e., layers), such as 2, 3, 4, 5, 6, 7, 8, 9, 10, or more plies. In one embodiment, the absorbent layer is folded to provide multiple plies. For example, the absorbent layer can be folded to provide three plies. When multiple plies are provided, the plies can all have the same thickness, each ply can have a different thickness, or some plies can have the same thickness while others have different thicknesses. Each ply can have a constant thickness or a variable thickness. Additionally, the plies can all be made up of the same material or of different materials. Each ply itself can also be made up of more than one material, such that the materials are non-homogeneously distributed. For example, a unitary (single) but non-homogenous absorbent layer or ply can have a portion that comprises fluff without SAP and another portion that comprises fluff with SAP, and optionally another portion that comprises fluff with a different proportion of SAP relative to fluff. A multicore, or ply, design of the absorbent core is discussed in co-pending international application titled "Multi-Core Absorbent Article", having application no. PCT/US2016/012710, and filed Jan. 8, 2016, the content of which is incorporated by reference herein in its entirety.

The back sheet 22 may generally extend over all or at least a portion of the undergarment 10, wherein the back sheet 22 provides a garment-facing surface of the undergarment when the undergarment is worn under clothing. The back sheet 22 can be joined to the fluid impervious barrier 21 (when present), via an adhesive 28. The adhesive can be, but is not limited to, an elastomeric adhesive, or a construction adhesive, such as the 5-5603 olefin adhesive also from H.B. Fuller Company.

The fastening system of the absorbent article shown in FIG. 4 includes tabs 12, which are secured via adhesive 42. It is to be understood that underwear-type disposable absorbent articles need not include tabs and can instead include a bond, such as an ultrasonic bond along the side edges of the front and rear sections when folded in half.

Optionally, the undergarment 10 may include a stand-up leg elastic assembly 36, including a nonwoven material, one or more elastic components 38, and an adhesive 40. Additionally, leg elastics 52 and leg elastic adhesives 50 may be layered generally between the back sheet 22, the polymeric barrier layer 21, and respective left and right side tabs 12. The leg elastics 50 may extend substantially parallel to a longitudinal axis of the undergarment 10 at or near leg cutouts. Additional exemplary absorbent articles and methods include, but are not limited to, those disclosed in U.S. Patent Application Nos. 62/407,152; 62/407,161; 61/705,802; Ser. No. 14/037,093; 61/884,697; Ser. No. 15/026,100; 62/101,469; 62/310,005; 62/337,111; 62/432,851; 62/449,388; and 62/432,729, all of which are incorporated herein by reference.

Figure 5:
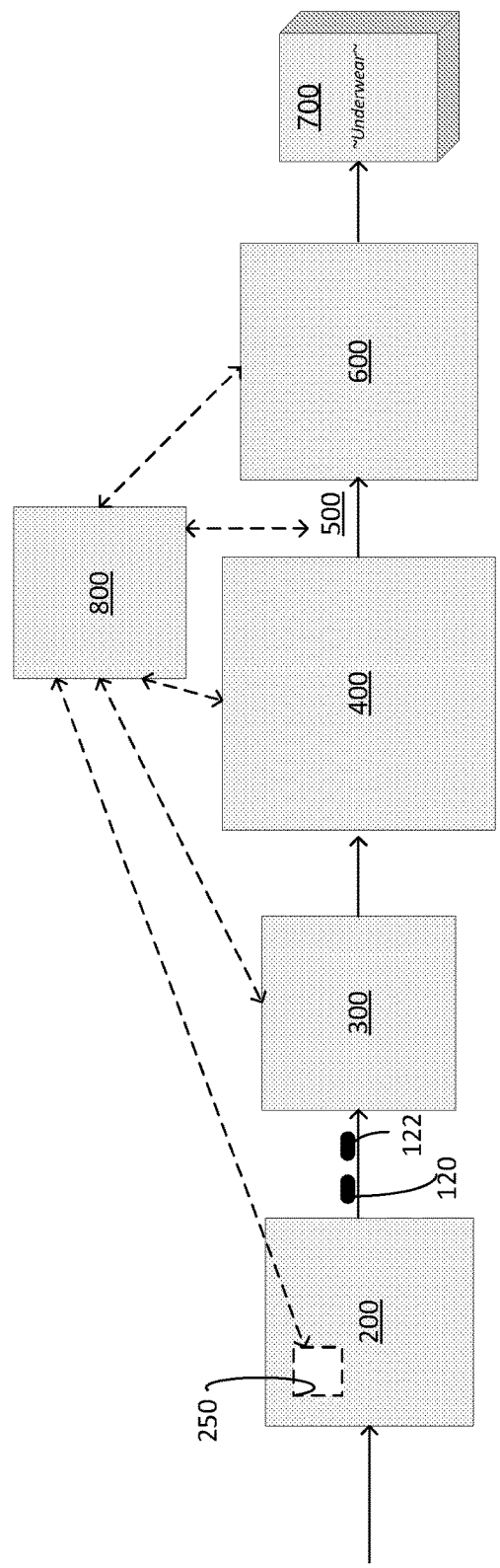
FIG. 5 is a schematic view of an absorbent manufacturing apparatus for printing and producing disposable absorbent articles in accordance with the present disclosure.
Figure 6:
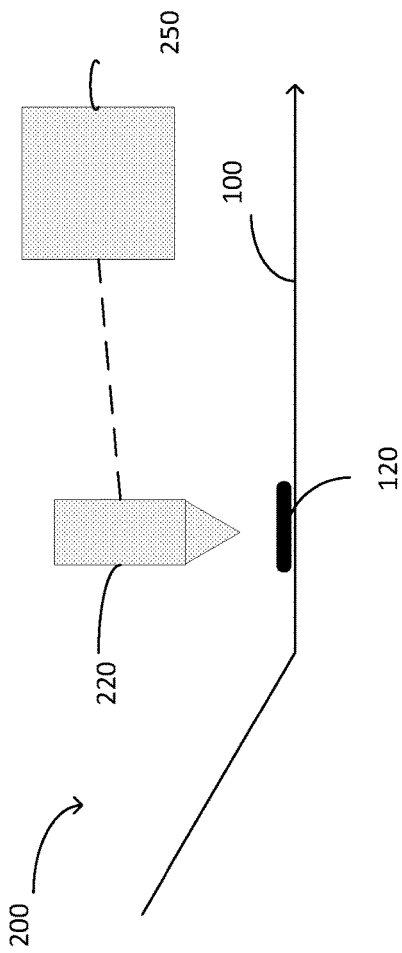
FIG. 6 is a schematic view of a printing system for printing images on a substrate in accordance with an embodiment of the present disclosure.

Generally, methods of the present disclosure include the printing of different images and/or the insertion of extra layers of absorbency at various intervals during the manufacturing process to produce absorbent articles having different images and/or varying absorbent levels interspersed throughout the same manufacturing run. However, the printing of different images and/or the insertion of different absorbency level absorbent cores are only part of a larger absorbent article manufacturing process. For example, FIG. 5 shows a schematic of a manufacturing process and corresponding apparatus for producing absorbent products in accordance with one embodiment. According to the embodiment, one or more substrates (FIG. 5 depicts a single substrate) pass through a printing system 200, wherein the images are printed on the surface of the substrate. As generally shown in FIG. 6, printing involves the steps of providing a substrate 100 moving in a web direction on the manufacturing line and printing the images on the substrate 100 using a printing system 200 as the substrate 100 continues moving in the web direction. The printed substrate continues advancing in the web direction and optionally passes through a curing system 300 for drying the ink on the substrate 100.

Subsequent to the printing 200 and curing systems 300, the substrate will continue through production system 400 wherein several different manufacturing processes occur to product discrete absorbent articles, such as forming, cutting, placing, combining, bonding, etc using various tools including, but not limited to: fluff forming wheels; web cutting tools such as flex knifes, slitters, die rolls, and lasers; compression and embossing systems; folding tools, such as longitudinal folders, and cross-folding systems; turning devices; slip-cut units; bonding units, such as thermal bond units, ultrasonic bond units, hot-melt bond units, and mechanical bond units; and liquid application tools. With specific respect to the present disclosure, these processes include the forming, cutting, and/or placing of different absorbent cores, as will be described in more detail below.

It is also to be understood that the order of the different processes and/or systems can vary. For example, in another embodiment, the printing and curing can occur after one or more manufacturing processes, such as after the cutting and placing of absorbent cores, etc. In yet another embodiment, the printing and curing can occur after all of the manufacturing processes, but before post-production wrapping, stacking packaging, etc.

Once the discrete absorbent articles are produced, they can be transported via the use of a conveyor 500 from the production system 400 to downstream operations in a post-production system 600. The post-production system 600 includes various tools and apparatuses for wrapping, stacking, packaging, etc. the absorbent articles to provide a final packages product 700 to be sold.

One or more controllers 800 can be communicatively coupled to any one or more of the printing system 200 (via the print controller 250), curing system 300, production system 400, the conveyor 500, and the post-production system 600, including any devices and/or tools within each of the systems, among other devices/tools. The controller 800 provides data/instructions to the systems and devices with respect to the operation of each. The controllers 250 and 800 can be coupled to the respective systems/devices via wireless or wired coupling.

Figure 7A:
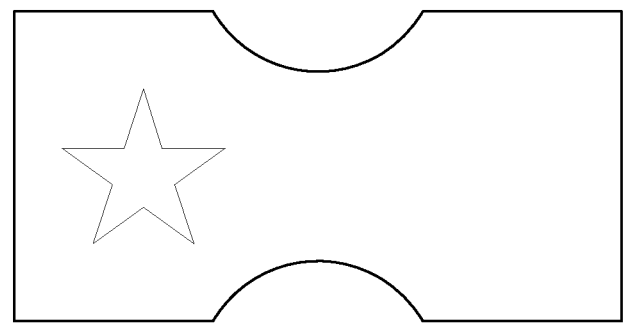
FIGS. 7A-C depicts different images that can be printed on an absorbent article.
Figure 7B:
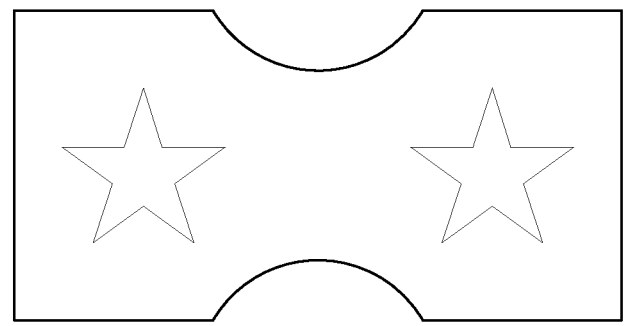
Figure 7C:
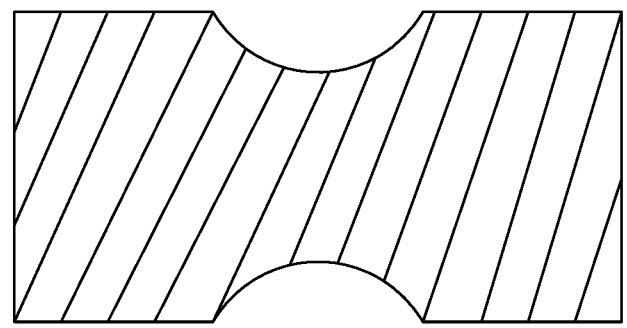

In accordance with certain embodiments of the present disclosure, such as to differentiate the products and/or for aesthetic purposes, the disposable articles include printing over all or a portion of the surface of a substrate, such as one or both of the top sheet or the back sheet, as shown in FIGS. 7A-C. In FIGS. 7A and B, images (shown as one and two stars here for illustration) are printed on a portion of a surface of the absorbent article. In FIG. 7C, the printed image occupies the entire surface (e.g., a color printed over the entire surface of the absorbent article). The printed image can include any one or more of graphic designs (e.g., patterns, characters, logos, shapes, etc.), size indicia, colors, or other markings for aesthetic or functional purposes. It is to be understood that for the purposes of this disclosure, one image includes any number of patterns, designs, colors, etc. printed on a single absorbent article (e.g., one product having a pitch length between two consecutive pitch intervals, as described in more detail below). For example, the two stars shown in FIG. 7B would be considered "one image" for the purposes of this disclosure.

Methods of the current invention involve the printing of various images on a substrate, such as a top sheet 18 or back sheet 22, during a disposable absorbent article manufacturing process. Both the top sheet 18 and the back sheet 22 have a body-facing side and a garment facing side. Print can be applied to either or both sides of either or both of the back sheet and the top sheet. In one example, the garment-facing side of the top sheet 18 serves as a substrate on which one or more images are printed. Because most top sheets 18 are thin and transparent, print can be easily seen through the top sheet 18 from the body-facing side. By printing on the side opposite of the body-facing side, the ink is not in direct contact with the user, which can be a safety concern. The substrate can be, for example, any material that is preferably in the form of a continuous web that is suitable for printing on a surface of at least one of its opposite sides. In one aspect, the material can include a woven material, nonwoven material, a film, a tissue wrap, an airlaid material, or any combinations thereof. In one embodiment, the substrate includes a non-woven material, such as an SMS material. The substrate can include one or more layers. The substrate is not limited to a top sheet and/or a back sheet, and can be any part of the absorbent article, such as, but not limited to, the absorbent core, a tab, or any combination thereof. In one embodiment, methods can involve the printing of two substrates in one manufacturing process.

Any number of different images can be printed on the substrate during the manufacturing process. For example, 1, 2, 3, 4, 5, 6, 7, 8, 9, 10, 15, 20, 25, 30, 35, 40, 45, 50, or more (and any number in between) images, can be printed on the substrate in the same manufacturing run. These different images can include different colors and/or print patterns.

In one embodiment, the images can include different colors to be printed on a portion of all of each absorbent article. For instance, the surface of the absorbent article, such as disposable underwear, facing away from the wearer can be printed using any number of colors, such as blue, grey, orange, green, skin-colored, black, pink, purple. Certain colors can be packaged together and be marketed to targeted consumer populations, such as one set of colors for women and another set for men. Popular colors for women tend to be black and tan-colored. Accordingly, it is possible to provide a multi-color pack of absorbent articles that includes, for example, any combination of a certain number of black disposable absorbent articles, tan-colored disposable absorbent articles, and white disposable absorbent articles. Thus, in accordance with methods of the present invention, a first image can include a first color (e.g., black), a second image can include a second color (e.g., tan), a third image a third color (e.g., pink), etc. The images can be printed between consecutive print intervals in accordance with methods of the invention.

Alternatively or additionally, the absorbent articles can include any number of different patterns. For example, print patterns of different sport objects can be added to the absorbent articles, such as football, baseball, basketball, soccer ball, tennis ball, etc. The logos and/or names of different sports teams (e.g., NFL, MLB, NBA, WNBA, NHL, MSL, etc.) can also be printed on the absorbent articles, taking into consideration any licensing fees and requirements that must be paid or met, respectively. Other patterns such as lace, hearts, flowers, leaves, polka dots, chevron patterns, butterflies, and ribbons can also be added. The present apparatuses and methods allow for any number of patterns, each article having the same or different pattern, to be consecutively printed and automatically packaged into one unit for sale.

With respect to children's disposable absorbent articles, such as diapers and training pants, different characters that can be licensed can be printed on the articles, such as Disney® characters (e.g., Mickey & Minnie Mouse, Pluto, Goofy, Donald Duck, Bambi, Jumbo, Peter Pan, Tinker Bell, Snow White, Cinderella, Pocahontas, Winnie the Pooh, Beauty & the Beast, Lion King, Toy Story, Cars, Aladdin, Hercules, Little Mermaid, Lady & the Tramp, Tarzan, Jungle Book, etc.), Looney Tunes® characters (e.g., Bugs Bunny, Daffy Duck, Tweedy, Tasmanian Devil, Sylvester, Porky Pig, Elmer Fudd, Pepe Le Pew, Speedy Gonzales, Yosemite Sam, Marvin the Martian, Foghorn Leghorn, Granny, Penelope Pussycat, etc.), Sesame Street® characters (e.g., Elmo, Big Bird, Cookie Monster, Bert, Ernie, Grover, Oscar the Grouch, Count von Count, Kermit the Frog, Miss Piggy, Mr. Snuffleupagus, Hoots the Owl, Abby Cadabby, Two-Headed Monster, etc.), super heroes, including Marvel® characters (e.g., Spider Man, Iron Man, Captain America, Hulk, Thor, Avengers, Daredevil, Superman, Batman, Robin, Thing, Green Lantern, Flash, Fantastic Four, Aquaman, Wolverine, Hawkman, Ninja Turtles, Power Rangers, Superwoman, Supergirl, Batgirl, Black Widow, Catwoman, Wonderwoman, Wonder Girl, Spider-Woman, Invisible Woman, Vixen, etc.), Barbie® characters, American Girl doll characters, etc. Other images for children can include, but are not limited to, dinosaurs, trains (i.e. Thomas the Tank Engine®), trucks (i.e. fire trucks), cars (i.e. police cars), earth-moving equipment (i.e. bulldozers), teddy bears, cats, dogs, unicorns, ponies, butterflies, rabbits, lambs, monkeys, koala and panda bears, etc. Using methods of the present disclosure, for example, any number of characters from one or more Disney movies can be consecutively printed and automatically packaged into one packing unit for sale (e.g., one bag or box of training pants can include a different Disney's Little Mermaid character on each training pant— Ariel, Prince Eric, Ursula, Sebastian, Flounder, King Triton, Grimsby, Scuttle, Attina, Aquata, Chef Louis, Max, etc.).

In another embodiment, the images can include the type of product (e.g., Night or Day absorbency levels) and/or the size (e.g., Small S, Medium M, Large L, etc.). The absorbent article may also optionally include a wetness indicator that can be printed on a substrate, to be positioned substantially centrally along a portion of a length of the absorbent article.

Generally, printing involves the steps of providing a substrate 100 moving in a web direction at a certain velocity on the manufacturing line and printing the images on the substrate 100 as it continues moving in the web direction, as shown in FIG. 6. Each image is disposed on the substrate between consecutive pitch intervals. This is illustrated in FIG. 8, which is a schematic representation of the substrate 100 moving in the machine direction, the substrate 100 having been printed with first and second images 120, 122, the images separated by and disposed in between consecutive pitch intervals P.

Figure 8:
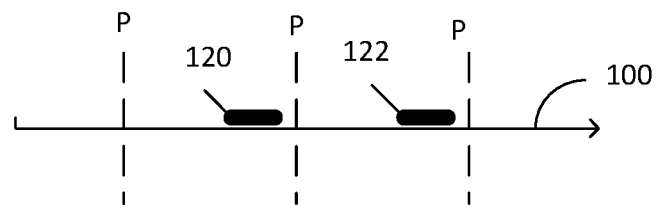
FIG. 8 depicts a schematic view of a first and second image printed on a substrate and separated by pitch intervals.
Figure 9:
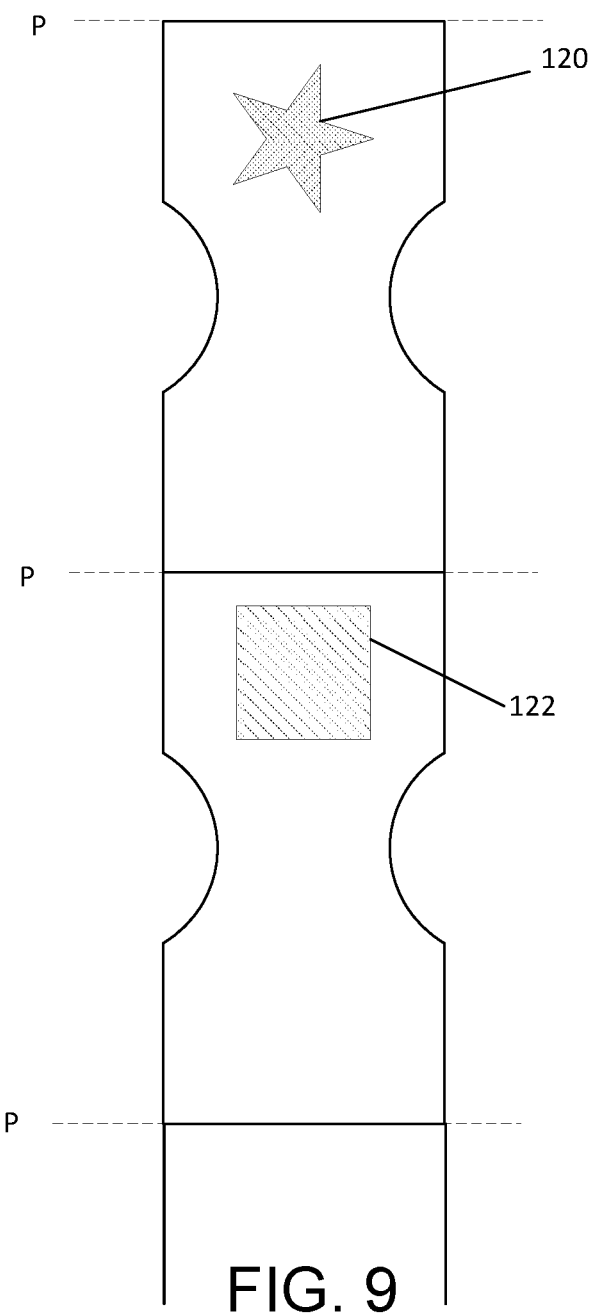
FIG. 9 shows a top plan view of the printed substrate of FIG. 13 with a first and second image separated by pitch intervals.

When different images are to be printed on the substrate 100 in order to provide absorbent articles bearing different images, the different images can be printed on the substrate 100 within consecutive pitch intervals, such that no blank space is needed in between pitch intervals P, as shown in FIG. 8. Additionally, FIG. 9 shows a top down view of the substrate 100 having different images printed thereon, the images 120, 122 printed within consecutive pitch intervals.

Figure 10:
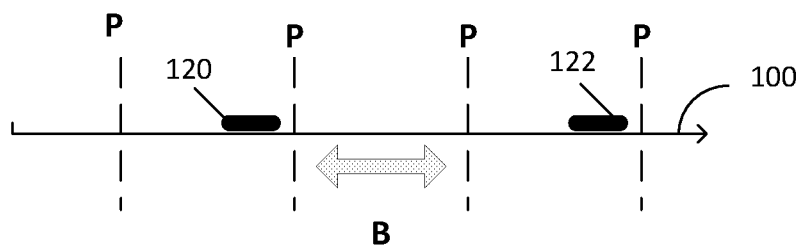
FIG. 10 depicts schematic view of a first and second image printed on a substrate and separated by a blank space in between pitch intervals.
Figure 11:
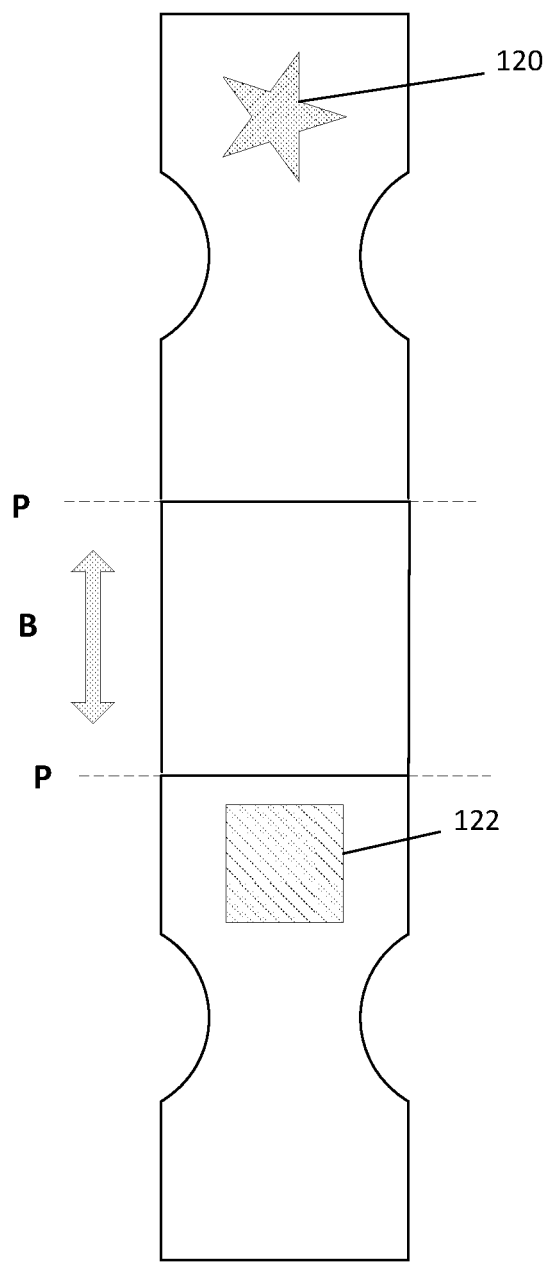
FIG. 11 shows a top plan view of the printed substrate of FIG. 15 with a first and second image separated by a blank space in between pitch intervals.

Prior methods involving printing different images in-line have required a black space on the substrate in between images. The requirement of the blank space between different images contributes to excess loss, materials, and cost. FIG. 10 is a schematic representation of the substrate 100 moving in the web direction, the substrate 100 having been printed with different images (e.g., first image 120 and second image 122), the different images separated by a blank space B, shown here, for example, as spanning one pitch length. Similarly, FIG. 11 shows a top plan view of the printed substrate of FIG. 10 with a first and second image separated by a blank space spanning one pitch length. However, it is to be understood that the blank space can be, and usually is, larger than one pitch length. Because of the need for blank space between different images, prior methods involved the printing of a large number of a first image before switching to a second image, wherein a large number of the second image would then be printed. Otherwise, the waste and cost attributed to the blank spaces needed between images would be unmanageable. Apparatuses and methods of the present disclosure eliminate the need for the blank space in between different images. This allows for any number of different images to be printed in consecutive order without needing to sacrifice substrate between one or more pitch intervals.

It is to be understood the manufacturing process can include the provision of any number of substrates to be printed on, such as 2, 3, 4, 5, or more substrates. As with the first substrate, each of these substrates are to be divided by pitch intervals and the images are to be printed between each consecutive print interval as the substrate moves in the web direction. A separate printing system for each substrate can be used. In one embodiment, the first substrate 100 is the back sheet 22 and the second substrate is the top sheet 18, both of which are to be printed.

Printing systems in accordance with the present invention can print images using ink or dyes. Preferably, the printer system of the present disclosure use ink-based systems, such as solvent or pigment-based inks. In certain embodiments pigment-based ink is preferred due to its ability to provide scratch, fade and water resistance. Exemplary inks include, but are not limited to, water-based pigment inks, such as those available from KODAK—the S-Series Packaging Inks in Cyan, Magenta, Yellow, and Black (CMYK, respectively).

In one aspect, the printing system is an inkjet-based system. Inkjet technology involves the propelling of droplets of ink onto a substrate. In one embodiment, the printing system utilizes a stream inkjet system, such as KODAK's Stream Inkjet Technology, which involves the flowing of inks under high pressure to produce an enormous stream of drops while heaters warm the surface of the fluid jet causing a mini-disturbance that breaks the stream into droplets.

The printing system 200 to be used in accordance with the present disclosure can include a plurality of printheads, in which the printheads can be grouped into sets. For example, one, two, three, four, five, six, seven, eight, nine, ten, or more printheads can be included in a single set of printheads. In one embodiment, each printhead delivers a single color. For example, in order to enable CMYK printing, four printheads—each comprising one of four colors C, M, Y, or K—could be combined. The printheads can be aligned with each other in the cross-direction of the substrate (as opposed to the web/machine direction) to comprise a set. It is to be understood that the printheads can be aligned in any desired manners.

Figure 12A:
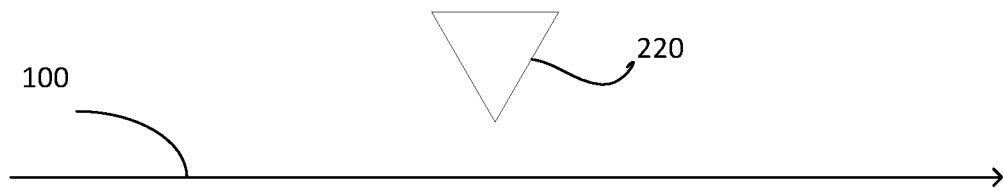
FIGS. 12A-C are schematic views of a substrate moving in the web, or machine, direction past one or more sets of printheads.
Figure 12B:
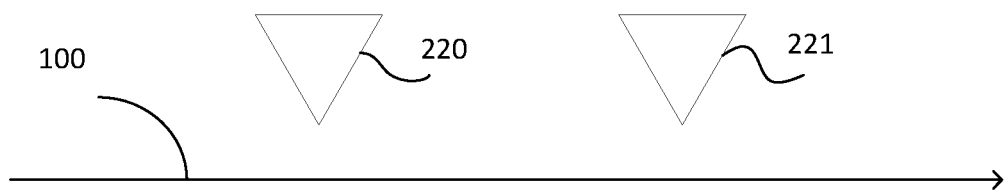
Figure 12C:
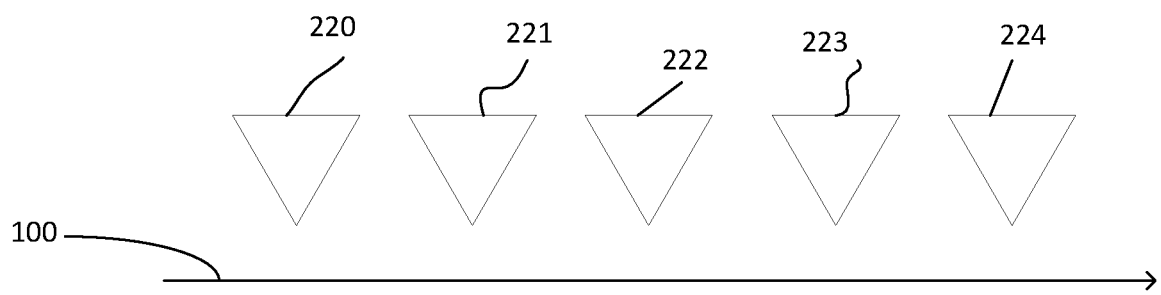

In one embodiment, all of the images are printed using a single set of printheads 220, as shown in FIG. 12A. In another embodiment, two sets of printheads 220, 221 are used to print the images, as shown in FIG. 12B. In yet other embodiments, 3 or more sets of printheads are used to print the images (e.g. 5 sets 220, 221, 222, 223, and 224, as shown in FIG. 12C). The printhead sets can be used in a number of ways to print the different images. For example, the first image can be printed using the first set of printheads 220 and the second image can be printed using the second set of printheads 221. In another example, one set 220 can print a color that covers the entire absorbent article (i.e. one pitch length spanning between two pitch intervals), and the other set 221 can print a pattern on the same absorbent article. In one example, such as when only one printhead is present in a set, each successive printhead can print a different color within the same registered or continuous print pattern when the desired image includes multiple colors in a single pattern, such that each absorbent article is printed with the same image. In yet another example, each successive printhead can print the same pattern but in a different color, such that each consecutive absorbent article has the same pattern but in a different color and thus, each consecutive absorbent article has a different image printed thereon. In still another example, a different pattern (e.g., character, shape), each optionally having different colors, can be consecutively printed on the substrate 100, separated by pitch intervals, with each character having been printed by a different set of printheads.

In addition to being able to print different colors and patterns, multiple sets of printheads allows for one or more printhead to be turned off while one or more are in operation. This allows for service or maintenance to be done on the printers without needing to stop the manufacturing process.

The printhead sets are spatially separated from each other in the web direction. This can be seen in FIGS. 12B and 12C, wherein the second set of printheads 221 is spaced apart from the first set of printheads 221 moving in the web direction WD, the third set 222 is spaced apart from the second set 221 moving further in the web direction, etc.

In operation, the printheads are controlled by one or more print controllers 250, which are in turn connected to one or more controllers 800 for the manufacturing line (see FIGS. 5 and 6). By connecting the print controller(s) 250 to the manufacturing line controller(s) 800, printing operations are effectively coordinated with the remainder of the manufacturing operations. In this manner, the printing can be coordinated with the manufacturing process, for example to coordinate printing with the velocity at which the substrate is traveling. Signals will be output from the manufacturing controllers 800 to the print controllers 250 with respect to the velocity. In some embodiment, the velocity can be determined with respect to any reference that can represent the velocity of the substrate 100 (e.g., a pitched unit operation, such as a cutting device, a discrete patch placing device, turning device, etc). The controllers send signals to the printheads to start and stop printing, as well as data with respect to the image to be printed on the substrate(s). In one embodiment, printing is effectuated by sending a start signal from the print controller 250 to one or more sets of printheads 220. In the case of multiple printhead sets, start signals can be sent to the sets simultaneously or at different times in order to stagger printing.

Methods and systems of the present disclosure can print images at speeds at least about 200, 300, 400, 500, 600, 700, 800, 900, and 1,000 fpm, and any speed in between. Images printed at any of these speeds can have a resolution of up to about 200×200 dpi, 320×320 dpi, 360×360 dpi, 600×600 dpi, 720×720 dpi, 1000×1000 dpi, 1200×1200 dpi, 1400×1400 dip, and any resolution therebetween.

In one example, the printing system 200 is the Prosper S10 Imprinting System from Kodak. The system uses pigment-based ink and can enable CMYK printing with the use of 4 print heads. The system can include up to 12 print stations and 24 printheads. Each print station houses electronics and software that manage the pumps, valves, and filters for controlling various flows, such as ink flow. Each print station supports up to two Printhead Interface Controllers (PICs), which control operation of the printheads. Fluid, including ink, and electronics are passed from the print station to the PIC/printerhead through an umbilical cord. The Prosper S10 system can run at speeds up to 1,000 fpm at a resolution of 600×600×1 dpi.

In one aspect of the present disclosure, tension is provided to the substrate 100 as it moves in the web direction. The tension helps to provide the substrate 100 with a smooth surface for printing. Tension can be provided to the substrate in a number of ways. For example, but not limitation, tension can be provided from any combination of metering devices (e.g., an omega roll or an s-wrap device), drive units, and series of rollers.

In one embodiment, tension is provided by advancing the web (e.g., substrate 100) over a vacuum drum 230 as the substrate 100 is printed using one or more printhead sets. Examples of this can be found in FIGS. 13A and B, which are schematic representations of the substrate web 100 entering the vacuum drum 230 and passing through various sets of printheads (e.g., 220-225) before the web 100 exits the drum 230. Rollers 240 are used to guide the web 100 into and out of the vacuum drum 230.

Figure 13A:
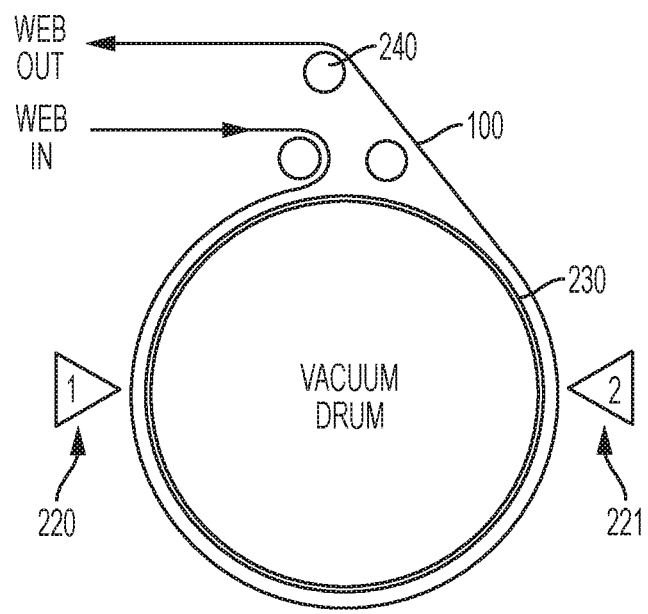
FIGS. 13A-B depict schematic views of the substrate being introduced to a vacuum drum and passing by two and six sets of printheads, respectively, as it continues moving at a velocity in the web direction.
Figure 13B:
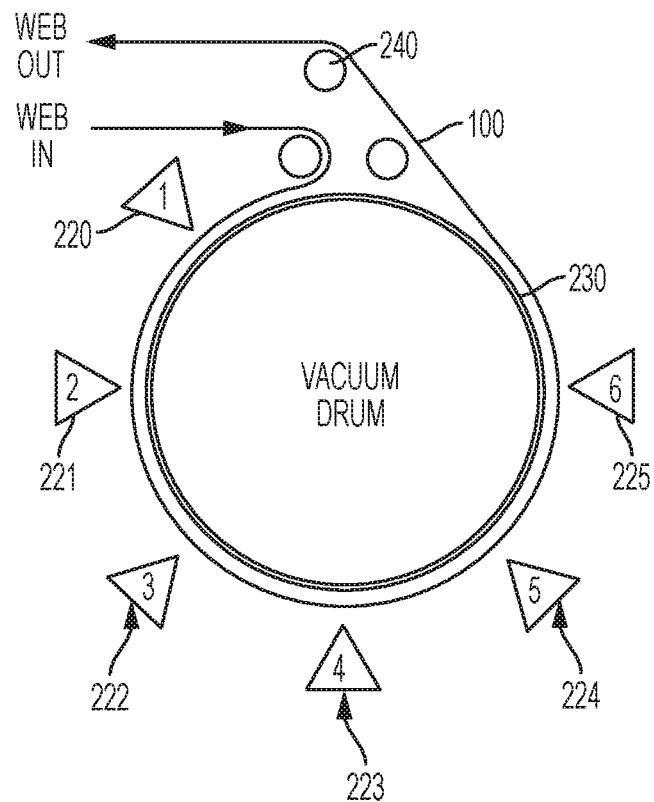

In embodiments wherein a vacuum drum 230 is used to provide tension to the substrate 100, the printheads will be positioned around the vacuum drum 230 such that each printhead extends in a radial direction from the vacuum drum 230. The printheads are preferably separated by a predetermined distance from the vacuum drum 230, as shown in FIGS. 13A and 13B. In the event that two or more sets of printheads (e.g., 220-225) are provided around the drum 230, each successive printhead set is spatially separated from the previous printhead set in the web direction, as also shown in FIGS. 13A and 13B. The printheads can be spatially separated by various distances, such as to be equidistantly spaced from each other, randomly spaced from each other, or any other spatial arrangement.

Methods also contemplate drying/curing the images subsequent to being printed. Curing will help to set the ink on the substrate. Curing can comprise any number of techniques, such as heating using convection and/or infrared technology, and UV radiation. In one embodiment, the image is cured by applying heat to the substrate using a curing system 300. An exemplary drying system that can be incorporated into the manufacturing process subsequent to the printing operation includes the Adphos NIR inkjet drying system.

In addition to printing (and optionally curing) one or more substrates, the substrates will undergo a number of additional operations, for example, in the production system 400, as indicated previously with respect to FIG. 5, such as the placement of the absorbent cores having varying absorbency levels (such as day and night protection or various "tiers" of absorbency), and the cutting of the substrate at pitch intervals, to produce discrete sheets (each sheet representing an absorbent article).

In certain embodiments, methods include the insertion of extra layers of absorbency at various intervals during the manufacturing process to produce absorbent articles having varying absorbent levels interspersed in the same manufacturing run. In one embodiment, the method includes the steps of providing a substrate (e.g., a back sheet optionally have a fluid impervious barrier affixed thereto) moving in the web direction at a first velocity, the substrate divided by pitch intervals, each pitch interval having a pitch length corresponding to a length or a width of an absorbent article prior to being cut; providing a first absorbent core to the substrate between a first pitch interval and a second pitch interval, the first absorbent core having a first absorbency level; and providing a second absorbent core to the substrate between the second pitch interval and a third pitch interval, the second absorbent core having a second absorbency level. It is to be understood that the present disclosure is not limited to two different absorbency levels and that any number of absorbency levels can be manufactured and packed together on the same line. For examples, two, three, four, five, six, or more absorbency levels can be manufactured and packaged in the same manufacturing process using the same line.

As described previously, the absorbent core 20 can comprise one or more layers. In some embodiments, a first absorbent article having first lower absorbency level can include an absorbent core having one, two, three, four, or more layers. A second absorbent article having an absorbency level higher than the first absorbent article can have one, two, three or more layers, in addition to the number of layers in the absorbent core of the first absorbent article. In other words, with each higher absorbency level absorbent article, the number of layers increases by at least one compared to the next lowest absorbency level absorbent article.

As provided previously, the layers can all be made up of the same material or they can be made up of different materials. Each layer itself can also be made up of more than one material, such that the materials are non-homogeneously distributed. In one embodiment, the composition of the layers in each of the absorbent articles having different absorbency levels are the same, with the higher absorbency level products having one or more additional layers compared to the lower absorbency level products. In another embodiment, the composition of the layers in the absorbent products are different such that the higher absorbency level product includes the same layers as the lower absorbency product, as well as additional layers comprising one or more different materials. In yet another embodiment, the layers in the higher absorbency level product are all different from the layers in the lower absorbency level product.

For example, the first absorbent article (lower absorbency level) can have a single layer absorbent core comprising pulp and SAP, while the second absorbent article (higher absorbency level) can have a dual layer absorbent core, each layer comprising pulp and SAP. In a second example, the first absorbent article (lower absorbency level) can have a dual layer absorbent core, each layer comprising pulp and SAP, while the second absorbent article (higher absorbency level) can have a triple layer absorbent core, each layer comprising pulp and SAP. In a third example the first absorbent article (lower absorbency level) can have a single layer absorbent core comprising an airlaid material, while the second absorbent article (higher absorbency level) can have a dual layer absorbent core, each layer also comprising an airlaid material. In a fourth example, the first absorbent article (lower absorbency level) can have a dual layer absorbent core each comprising an airlaid material, while the second absorbent article (higher absorbency level) can have a triple layer absorbent core, each layer also comprising an airlaid material. In a fifth example, the first absorbent article (lower absorbency level) can have a single layer absorbent core comprising pulp and SAP, while the second absorbent article (higher absorbency level) can have a single layer absorbent core, comprising pulp, SAP, and an airlaid material. In a sixth example, the first absorbent article (lower absorbency level) can have a dual layer absorbent core, each layer comprising pulp and SAP, while the second absorbent article (higher absorbency level) can have a dual layer absorbent core, each layer comprising pulp, SAP, and an airlaid material. It is to be understood that the above embodiments are only provided as examples and not meant to be limiting. The absorbent cores can be any combination of the above materials, or any other material.

In embodiments wherein different prints and/or colors are provided to the absorbent articles, the different prints/colors can be used for aesthetic purposes and/or to help differentiate the different absorbency level products from one another. For example, the higher absorbency level product can have a first image printed on its surface, while the lower absorbency level product has no image or a second image printed on its surface, such that the two absorbency level products are easily distinguishable from each other.

In one embodiment, the products are marked to indicate the type of product (e.g., Night or Day absorbency levels) and/or the size (e.g., Small S, Medium M, Large L, etc.). The products can be marked by direct printing as discussed above, by using a label (which can be printed), or by any other means known in the art. For example, a label can be added to the absorbent article via any means known in the art. In one embodiment, the label can be printed onto one or both of the top sheet and the back sheet, such that the label is visible from the inside and/or the outside (preferably the back portion). In another embodiment, the label can be a pre-printed label and can be affixed to the absorbent article via any means known in the art such as, but not limited to, adhesive and bonding. In one embodiment, the label is adhered using a hot melt adhesive. In another embodiment, the label is adhered using one or more ultrasonic bonds.

Figure 14:
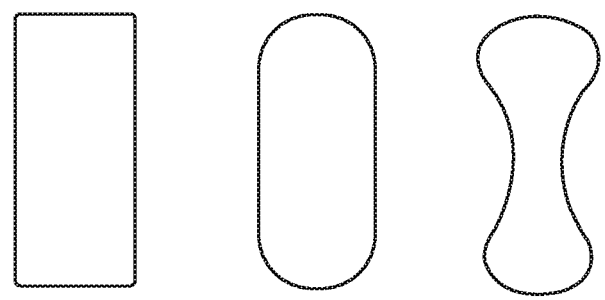
FIG. 14 displays three different exemplary absorbent core shapes.
Figure 15A:
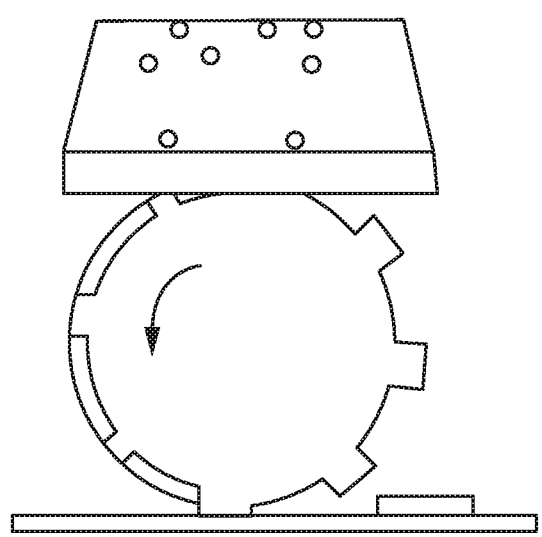
FIG. 15A is a schematic view of a forming wheel for producing absorbent cores.
Figure 15B:
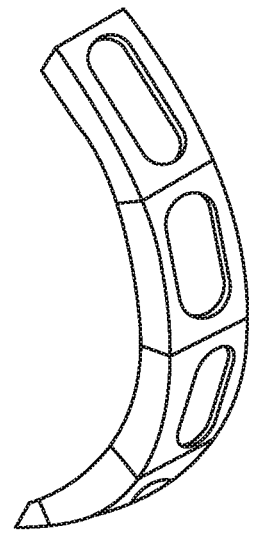
FIG. 15B is a partial view of the outside surface of the forming wheel of FIG. 15A showing the molds for the absorbent core.
Figure 16:
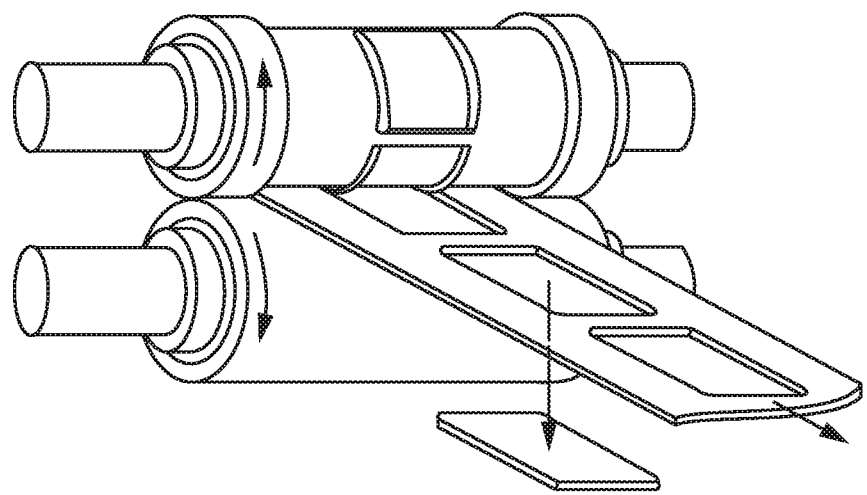
FIG. 16 shows dual drum die cutter for cutting and placing the absorbent from a continuous web substrate.

In addition to different levels of absorbency, the absorbent core can be formed into different shapes, such that two consecutive absorbent articles can have a different core. For example, see FIG. 14, which shows three different non-limiting exemplary core shapes. It is to be understood that the invention is not limited to these shapes and that any other shape, similar or different, can be used in accordance with the present disclosure. These shapes can be cut and placed using, for example, a forming wheel, such as those shown in FIGS. 15A and 16. FIG. 15A shows a forming wheel in which pulp and/or SAP can be fed into a fixed-rotor mill assembly, wherein a vacuum drum draws the pulp from the mill. The vacuum drum can include shaped pockets of different depths, such that the product exits the drum as discrete absorbent core elements. FIG. 15B shows a cutaway view of an exemplary surface of a vacuum drum for forming oblong shaped absorbent cores. FIG. 16 shows dual drum die cutter for cutting and placing the absorbent from a continuous web substrate. Although shown here as either oblong or rectangular shape, the absorbent core shape can be any shape. Additionally, the forming wheels/dies can include shaped pockets/dies of multiple shapes in any desired sequence. For example, the shape sequence can be such that one core is hourglass shape, the next is rectangular, then hourglass, then rectangle, and so on. In some embodiments, the shape of the core is chosen depending on the purpose for which the absorbent article will eventually be used. For example, an hour glass shape is typically preferred for nighttime wear given that it fits more closely with the anatomy of the user and provides better absorbent coverage when the individual is situated in different positions during sleep, while a rectangular shape can be used for day time wear.

Figure 17:
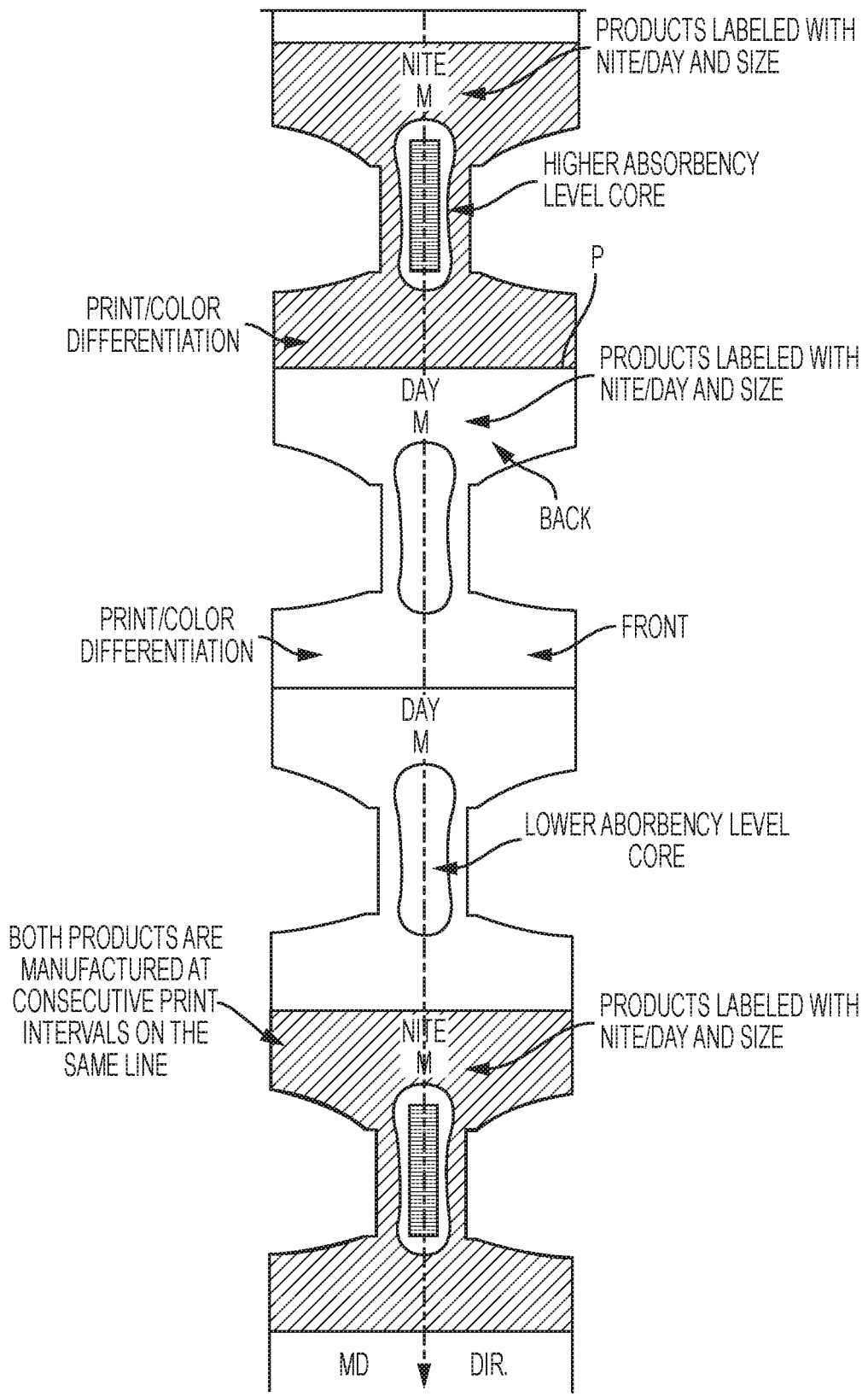
FIG. 17 is a top plan view of a printed substrate having consecutively aligned absorbent articles differentiated from one another by color/pattern and absorbency level.

FIG. 17 shows a top plan view of a substrate divided by pitch intervals P and having different absorbent articles in consecutive alignment. As can be seen, two different absorbent articles are arranged consecutively with one another, such that a first absorbent article having a higher absorbency level core and a first pattern and/or color is consecutively aligned with a second absorbent article having a lower absorbency level core and a second pattern and/or color (or no color). The absorbent articles are shown here arranged in a pattern with one higher absorbency level article to every two lower absorbency level articles. However, it is to be understood that any pattern can be used, such one higher absorbency level article to every one lower absorbency level article. Additionally, labels showing both the size and purpose of use have also been applied in FIG. 17.

Figure 18:
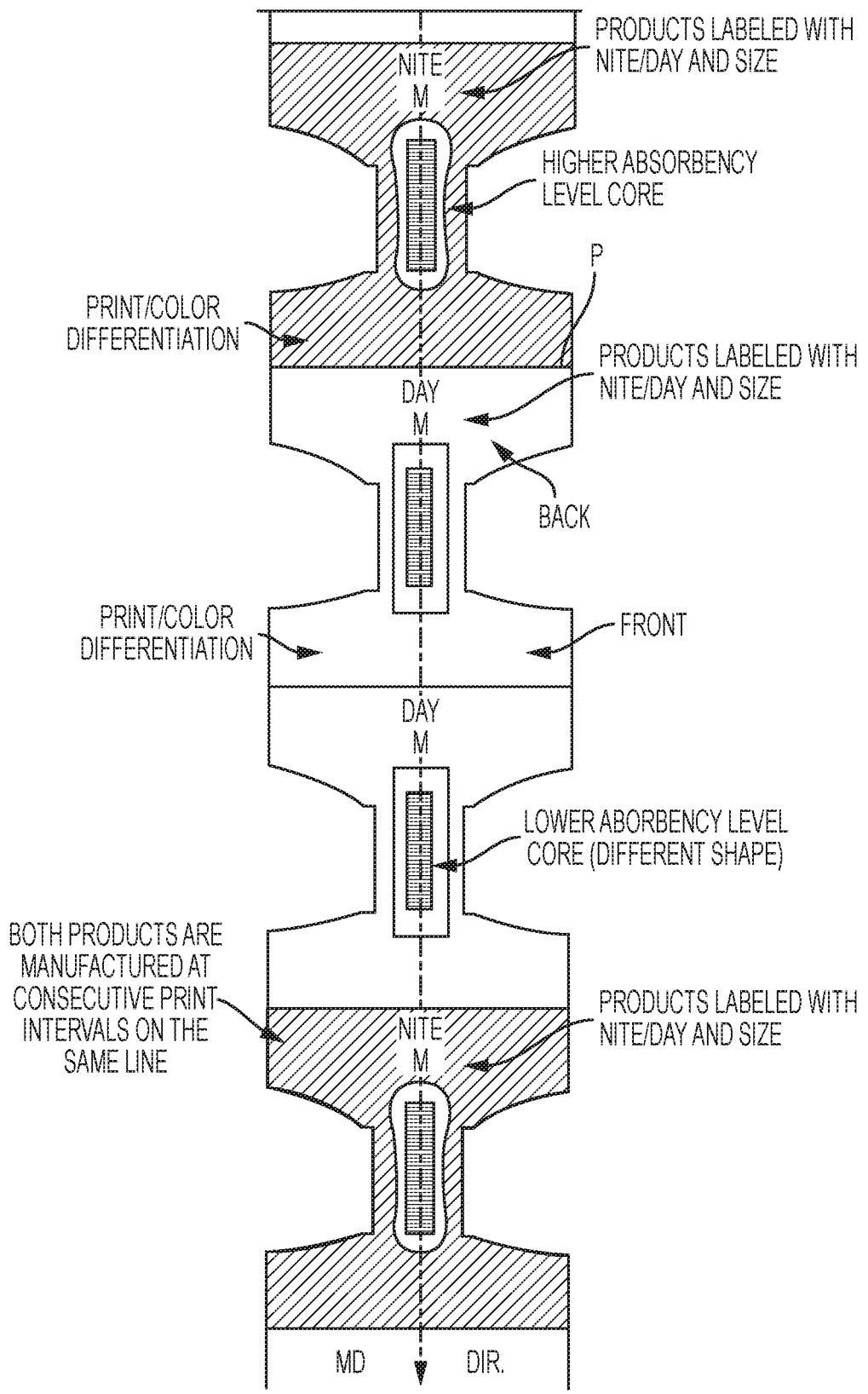
FIG. 18 is a top plan view of a printed substrate having consecutively aligned absorbent articles differentiated from one another by color/pattern, shape of absorbent core, and absorbency level.

Similarly, FIG. 18 shows a top plan view of a substrate divided by pitch intervals and having different absorbent articles in consecutive alignment. As can be seen here, in addition to different absorbency levels, labeling, and color/pattern differentiation, the shapes of the absorbent core are also varied between products with the higher absorbency product (NITE) having an hourglass shape core (DAY) and the lower absorbency product having a rectangular shaped core.

In some aspects, the pattern in which the absorbent articles are arranged can be chosen depending on the end purpose for which the articles will be sold. For example, the absorbent articles can be packaged in a combo pack for both day and night use, wherein daytime absorbency level articles are used more than nighttime absorbent articles. Accordingly, one package can have two day time absorbent articles to every one nighttime absorbent article (e.g., a 30 count bag would contain 20 daytime and 10 nighttime absorbent articles), consistent with FIGS. 17 and 18. In another example, a package can contain absorbent articles having two or more different absorbency levels (known as "tiers"), that would allow consumers to choose which article to wear based on the type of activity planned. For instance, a higher tier absorbent product would be desired for traveling while a lower tier absorbent product may be desired while playing a sport or when the individual is at home. In some packages, the amount of higher tier products can equal the amount of lower tier products. In other packages, the amount of higher tier products can be higher than the amount of lower tier products, and vice versa. However, the invention is not limited to these ratios. The absorbent articles can be produced and packaged in any ratio, for example at any ratio between about 10:1 and 1:10 for any two products in a package.

It is to be understood that other features & product attributes can be registered & applied to the products as well, in order to offer the consumer a variety of different products within the same bag, in accordance with the present disclosure. The key advantage of the methods, apparatuses and product lies in the ability to produce and package differentiated products inline at high production speeds. There is no need to repack the different products into one package, which is both highly time consuming and costly.

Figure 19:
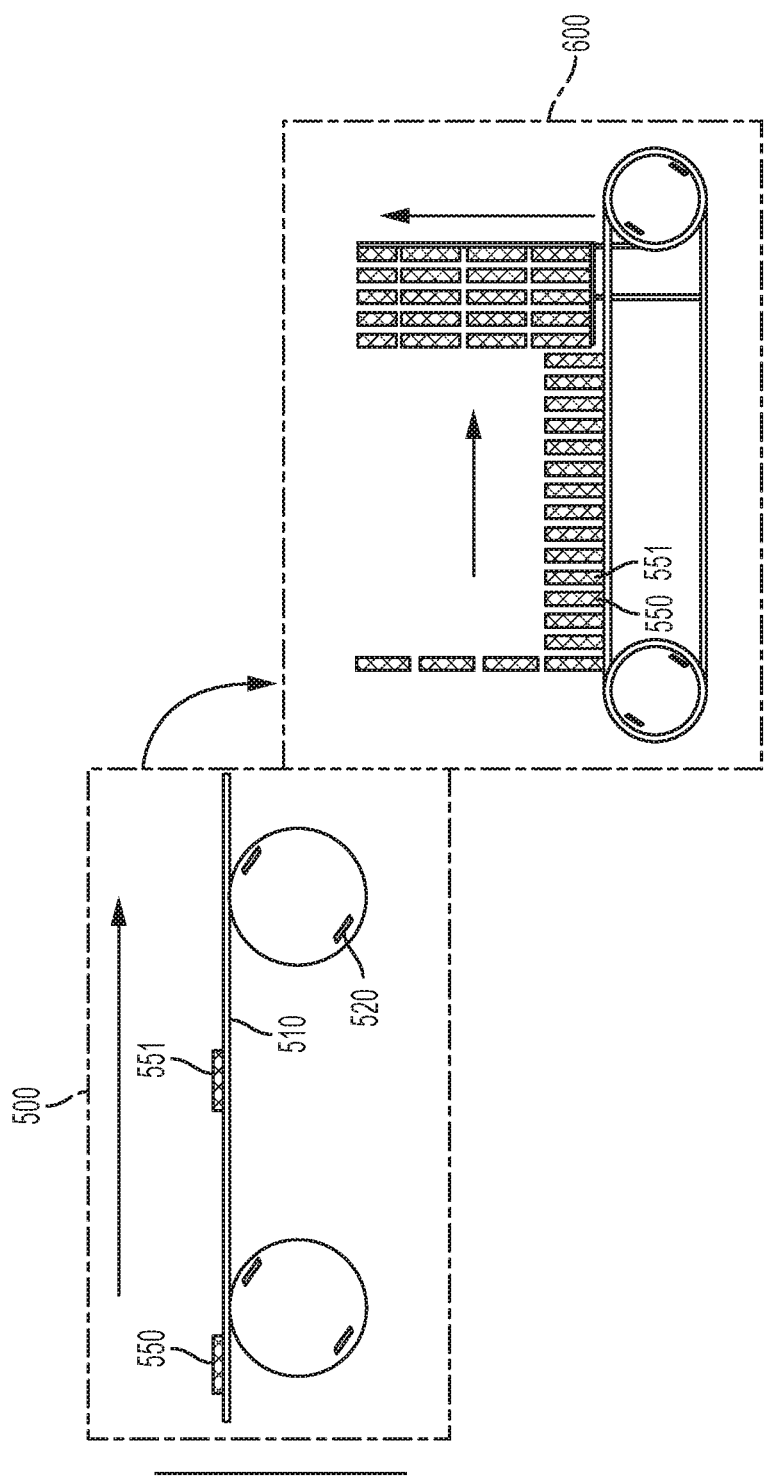
FIG. 19 depicts a schematic view of absorbent articles advancing along a conveyor belt to a stacking and packaging operation.

Subsequent to these operations, the discrete absorbent articles will be advanced along the manufacturing line using, for example, a conveyor belt 510, to downstream operations in the post-production system 600 that include folding, wrapping, stacking and packaging. FIG. 19 shows a schematic of a conveyor system 500, including a conveyor belt 510 and corresponding rollers 520, delivering a first absorbent article 550 comprising a first absorbency level and a first image and a second absorbent article 551 comprising a second absorbency level and a second image to the post-production system 600. As can be seen in FIG. 19, the discrete absorbent articles are lined up and packaged sequentially as they come off the conveyor belt, such that the first article 550 and the second article 551, each containing different absorbency levels and, optionally images, are automatically packaged in the same box or bag without need to repack the different products together.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for printing a surface of an absorbent article during an automated manufacturing process on a manufacturing line having at least one printer system configured to print two or more colors during the process, the method comprising:
   providing a first substrate moving in a web direction on the manufacturing line, the substrate divided into pitch intervals, each pitch interval having a pitch length corresponding to a length or a width of an absorbent article prior to being cut; and
   printing images on the substrate using the printer system as the substrate moves at a velocity in the web direction, each image separated by a pitch interval, wherein the images comprise at least a first image and a second image, and wherein the first image is printed between a first pitch interval and a second pitch interval and the second image is printed between the second pitch interval and a third pitch interval, wherein the first image comprises a first color and the second image comprises a second color.

2. The method of claim 1, wherein the first image comprises a first pattern and the second image comprises a second pattern.

3. The method of claim 1, further comprising providing tension to the substrate such that the substrate is provided with a smooth surface for printing as the substrate passes through the printer system and wherein providing tension comprises advancing the web over a vacuum drum as the substrate is printed.

4. The method of claim 1, wherein the substrate comprises a material selected from the group consisting of: a woven material, a non-woven material, a polymer-based film, a tissue wrap, and an airlaid material.

5. The method of claim 4, wherein the substrate comprises non-woven material, including a spunbond-meltblown-spunbond material.

6. The method of claim 5, wherein the substrate comprises any one of a top sheet of the absorbent article and a back sheet of the absorbent article.

7. The method of claim 1, wherein the first and second images are printed using one set of printheads.

8. The method of claim 1, wherein printing images comprises:
   printing the first image using a first set of printheads; and
   printing the second image using a second set of printheads.

9. The method of claim 1, wherein the images are printed using two or more sets of printheads, and
   wherein a first set of printheads is spatially separated from a second set of printheads in the web direction, and
   wherein printing images comprises sending a start signal from a print controller to the set of printheads, and
   wherein printing images comprises simultaneously sending a first start signal from the print controller to the first set of printheads and the second set of printheads, such that the first and second images are printed at the same time.

10. The method of claim 1, further comprising curing the images subsequent to being printed, wherein the curing comprises applying heat to the substrate.

11. The method of claim 1, further comprising cutting the substrate at the pitch intervals as the web advances to produce discrete absorbent articles, such that a first absorbent article comprises the first image and a second absorbent article comprises the second image; and further comprising:
   advancing the discrete absorbent articles along the manufacturing line to a packaging station; and
   packaging the discrete absorbent articles such that the first absorbent article comprising the first image is automatically packaged with the second absorbent article comprising the second image.

12. The method of claim 1, further comprising:
   providing a second substrate moving in the web direction, the second substrate divided by the pitch intervals;
   printing images on the second substrate using a second printing system, each image separated by the pitch intervals.

13. The method of claim 1, wherein the images are printed at a speed of at least 700 fom; or
   wherein the images have a resolution of at least about 600×600 dpi; or
   wherein the images are printed using at least one of a pigment-based ink and a solventbased ink, or wherein the printing system is a stream inkjet system.

14. The method of claim 1, further comprising:
   providing a first absorbent core to the substrate between the first pitch interval and the second pitch interval, the first absorbent core having a first absorbency level; and
   providing a second absorbent core to the substrate between the second pitch interval and the third pitch interval, the second absorbent core having a second absorbency level.

15. A method for printing a surface of an absorbent article during an automated manufacturing process on a manufacturing line having at least one printer system configured to print two or more images during the process, the method comprising:

providing a first substrate moving in a web direction on the manufacturing line, the substrate divided into pitch intervals, each pitch interval having a pitch length corresponding to a length or a width of an absorbent article prior to being cut; and printing images on the substrate using the printer system as the substrate moves at a velocity in the web direction, each image separated by a pitch interval, wherein the images comprise at least a first image and a second image, and wherein the first image is printed between a first pitch interval and a second pitch interval and the second image is printed between the second pitch interval and a third pitch interval, wherein the first image comprises a first color and the second image comprises a second color.

* * * * *